United States Patent
Li et al.

(10) Patent No.: US 10,222,346 B2
(45) Date of Patent: *Mar. 5, 2019

(54) DECOMPOSABLE S-TETRAZINE BASED POLYMERS FOR SINGLE WALLED CARBON NANOTUBE APPLICATIONS

(71) Applicant: NATIONAL RESEARCH COUNCIL OF CANADA, Ottawa (CA)

(72) Inventors: Zhao Li, Orleans (CA); Jianfu Ding, Orleans (CA); Patrick Roland Lucien Malenfant, Orleans (CA)

(73) Assignee: National Research Council of Canada, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/708,855

(22) Filed: Sep. 19, 2017

(65) Prior Publication Data
US 2018/0195997 A1 Jul. 12, 2018

Related U.S. Application Data

(63) Continuation-in-part of application No. 15/401,421, filed on Jan. 9, 2017.

(51) Int. Cl.
*C01B 32/159* (2017.01)
*G01N 27/414* (2006.01)
(Continued)

(52) U.S. Cl.
CPC ....... *G01N 27/4141* (2013.01); *C01B 32/159* (2017.08); *G01N 27/4146* (2013.01);
(Continued)

(58) Field of Classification Search
CPC ............. G01N 27/4141; C01B 32/159; C01B 2202/02; H01L 51/0048; H01L 51/0545;
(Continued)

(56) References Cited

U.S. PATENT DOCUMENTS

| 8,673,183 B2 | 3/2014 | Ding et al. |
| 2008/0287638 A1 | 11/2008 | Reynolds et al. |
| 2013/0253120 A1 | 9/2013 | Kulkarni et al. |

FOREIGN PATENT DOCUMENTS

| WO | 2015024115 A1 | 2/2015 |

OTHER PUBLICATIONS

Zhang, Ting, et al. "Electrochemically functionalized single-walled carbon nanotube gas sensor." Electroanalysis 18.12 (2006): 1153-1158.*

(Continued)

*Primary Examiner* — Richard M Rump
(74) *Attorney, Agent, or Firm* — Aventum IP Law LLP

(57) ABSTRACT

A process for purifying semiconducting single-walled carbon nanotubes (sc-SWCNTs) extracted with a conjugated polymer, the process comprising exchanging the conjugated polymer with an s-tetrazine based polymer in a processed sc-SWCNT dispersion that comprises the conjugated polymer associated with the sc-SWCNTs. The process can be used for production of thin film transistors and chemical sensors. In addition, disclosed herein is use of an s-tetrazine based polymer for purification of semiconducting single-walled carbon nanotubes (sc-SWCNTs).

8 Claims, 7 Drawing Sheets

(51) Int. Cl.
H01L 51/05 (2006.01)
H01L 51/00 (2006.01)
(52) U.S. Cl.
CPC ...... H01L 51/0048 (2013.01); H01L 51/0545 (2013.01); *C01B 2202/02* (2013.01); *H01L 51/0002* (2013.01); *H01L 51/0003* (2013.01); *H01L 51/0026* (2013.01); *H01L 51/0558* (2013.01)
(58) Field of Classification Search
CPC ............. H01L 51/0003; H01L 51/0558; H01L 51/0002; H01L 51/0026
See application file for complete search history.

(56) References Cited

OTHER PUBLICATIONS

Wongwiriyapan, Winadda, et al. "Single-walled carbon nanotube thin-film sensor for ultrasensitive gas detection." Japanese journal of applied physics 44.4L (2005): L482.*
Valentini, L., et al. "Highly sensitive and selective sensors based on carbon nanotubes thin films for molecular detection." Diamond and Related Materials 13.4-8 (2004): 1301-1305.*
Wei, Liangming, et al. "Hole doping and surface functionalization of single-walled carbon nanotube chemiresistive sensors for ultrasensitive and highly selective organophosphor vapor detection." Nanotechnology 22.42 (2011): 425501.*
Rigoni, Federica et al—"Enhancing the sensitivity of chemiresistor gas sensors based on pristine carbon nanotubes to detect low-ppb ammonia concentrations in the environment"; RSC Publishing, This journal is The Royal Society of Chemistry 2013, Analyst, 2013, 138, pp. 7392-7399.
Rother, Marcel et al—"Aerosol-Jet Printing of Polymer-Sorted (6,5) Carbon Nanotubes for Field-Effect Transistors with High Reproducibility"; Advanced Electonic Materials, 2017 Wiley-VCH Verlag GmbH & Co., Adv. Electron. Mater. 2017, 3, pp. 1700080-(1-9).
Shea, Matthew J. et al—"Experimental Measurement of the Binding Configuration and Coverage of Chirality-Sorting Polyfluorenes on Carbon Nanotubes"; ACS Publications, 2014 American Chemical Society; J. Phys. Chem. Lett. 2014, 5, pp. 3742-3749.
Stranks, Samuel D. et al—"Nanoengineering Coaxial Carbon NanotubeDual-Polymer Heterostructures", 2012 American Chemical Society, ACS Nano, vol. 6, No. 7, pp. 6058-6066.
Stranks, Samuel D. et al—"Novel Carbon Nanotube-Conjugated Polymer Nanohybrids Produced by Multiple Polymer Processing"; 2013 Wiley-VCH Verlag GmbH & Co., Adv. Mater. 2013, 25, pp. 4365-4371.
Stranks, Samuel D. et al—"Production of High-Purity Single-Chirality Carbon Nanotube Hybrids by Selective Polymer Exchange"; 2013 Wiley-VCH Verlag GmbH & Co., small 2013, 9, No. 13, pp. 2245-2249.
Sun, Dong-Ming et al—"A Review of Carbon Nanotube- and Graphene-Based Flexible Thin-Film Transistors"; 2013 Wiley-VCH Verlag GmbH & Co., small 2013, 9, No. 8, pp. 1188-1205.
Takenobu, Taishi et al—"Stable and controlled amphoteric doping by encapsulation of organic molecules inside carbon nanotubes"; 2003 Nature Publishing Group, nature materials, vol. 2, Oct. 2003, pp. 683-688.
Toshimitsu, Fumiyuki et al—"Semiconducting single-walled carbon nanotubes sorting with a removable solubilizer based on dynamic supramolecular coordination chemistry"; 2014 Macmillan Publishers Limited, Nature Communications, 5:5041 | DOI: 10.1038/ncomms6041, Published Oct. 3, 2014, pp. 1-9.
Toshimitsu, Fumiyuki et al—"Facile Isolation of Adsorbent-Free Long and Highly-Pure Chirality-Selected Semiconducting Single-Walled Carbon Nanotubes Using a Hydrogen-bonding Supramolecular Polymer"; www.nature.com/scientificereports, Scientific Reports | 5:18066; DOI: 10.1038/srep18066; Published: Dec. 14, 2015.

Tulevski, George S. et al—"Toward High-Performance Digital Logic Technology with Carbon Nanotubes"; 2014 American Chemical Society, ACS Nano vol. 8, No. 9, 2014—pp. 8730-8745.
Umeyama, Tomokazu et al—"Dispersion of carbon nanotubes by photo- and thermal-responsive polymers containing azobenzene unit in the backbone"; This journal is The Royal Society of Chemistry 2010, Chem. Commun., 2010, 46, pp. 5969-5971.
Wang, Wei Zhi et al—"Degradable Conjugated Polymers: Synthesis and Applications in Enrichment of Semiconducting Single-Walled Carbon Nanotubes"; 2011 Wiley-VCH Verlag GmbH & Co., Adv. Funct. Mater. 2011, 21, pp. 1643-1651.
Wang, Xuewen et al—"Reproducible layer-by-layer exfoliation for free-standing ultrathin films of single-walled carbon nanotubes"; RSC Publishing, This journal is The Royal Society of Chemistry 2012, J. Mater. Chem., 2012, 22, pp. 21824-21827.
Wang, Chuan et al—"Carbon nanotube electronics—moving forward"; RSC Publishing, This journal is The Royal Society of Chemistry 2013, Chem. Soc. Rev., 2013, 42, pp. 2592-2609.
Wang, Huiliang et al—"Conjugated polymersortingof semiconducting carbonnanotubes and their electronic applications"; 2015 Elsevier Ltd., Science Direct, Nano Today (2015) 10, pp. 737-758.
Wu, Yucui et al—"Carbon Nanotubes for Thin Film Transistor: Fabrication, Properties, and Applications"; Hindawi Publishing Corporation, Journal of Nanomaterials, vol. 2013, Article ID 627215, 16 pages.
Zhang, Ting et al—"Recent progress in carbon nanotube-based gas sensors"; 2008 IOP Publishing Ltd., doi:10.1088/0957-4484/19/33/332001, Nanotechnology 19 (2008) 332001 (14pp).
Zhang, Zengxing et al—"Reversible Dispersion and Release of Carbon Nanotubes Using Foldable Oligomers"; JACS, 2010 American Chemical Society, J. Am. Chem. Soc. 2010, 132,—pp. 14113-14117.
Zhang, Hongliang et al—"Separation and/or selective enrichment of single-walled carbon nanotubes based on their electronic properties"; This journal is The Royal Society of Chemistry 2011, Chem. Soc. Rev., 2011, 40, pp. 1324-1336.
Zhang, Qiang et al—"The Road for Nanomaterials Industry: A Review of Carbon Nanotube Production, Post-Treatment, and Bulk Applications for Composites and Energy Storage"; 2013 Wiley-VCH Verlag GmbH & Co., small 2013, 9, No. 8, pp. 1237-1265.
Zheng, Ming et al—"Enrichment of Single Chirality Carbon Nanotubes"; JACS, 2007 American Chemical Society, J. Am. Chem. Soc. 2007, 129, pp. 6084-6085.
Aguirre, Carla M. et al—"The Role of the Oxygen/Water Redox Couple in Suppressing Electron Conduction in Field-Effect Transistors"; 2009 Wiley-VCH Verlag GmbH & Co. KGaA, Weinheim, Adv. Mater. 2009, 21, pp. 3087-3091.
Arnold, Michael S. et al—"Sorting carbon nanotubes by electronic structure using density differentiation"; nature nanotechnology vol. 1 |Oct. 2006 | www.nature.com/naturenanotechnology, pp. 60-65.
Avouris, Phaedan—"Molecular Electronics with Carbon Nanotubes"; American Chemical Society, Accounts of Chemical Research / vol. 35, No. 12, 2002, pp. 1026-1034.
Brady, Gerald J. et al—"High performance transistors via aligned polyfluorene-sorted carbon nanotubes"; American Institute of Physics, Citation: Appl. Phys. Lett. 104, 083107 (2014); doi: 10.1063/1.4866577—pp. 083107-1 to 083107-5.
Brady, Gerald J. et al "Quasi-ballistic carbon nanotube array transistors with current density exceeding Si and GaAs"; Research Article; Sci. Adv. 2016; 2 : e1601240 Sep. 2, 2016, pp. 1-9.
Broza, Georg—"Synthesis, Properties, Functionalisation and Applications of Carbon Nanotubes: A State of the Art Review"; Chemistry & Chemical Technology, vol. 4, No. 1, 2010, pp. 35-45.
Cao, Qing et al—"Ultrathin Films of Single-Walled Carbon Nanotubes for Electronics and Sensors: A Review of Fundamental and Applied Aspects"; 2009 Wiley-VCH Verlag GmbH & Co. KGaA, Weinheim, Adv. Mater. 2009, 21, pp. 29-53.
Cao, Qing et al—"Evaluation of Field-Effect Mobility and Contact Resistance of Transistors That Use Solution-Processed Single-Walled Carbon Nanotubes"; ACS NANO—2012—vol. 6—No. 7 pp. 6471-6477.

(56) References Cited

OTHER PUBLICATIONS

Cao, Changyong et al—"Completely Printed, Flexible, Stable, and Hysteresis-Free Carbon Nanotube Thin-Film Transistors via Aerosol Jet Printing"; 2017 Wiley-VCH Verlag GmbH & Co. KGaA, Weinheim, Adv. Electron. Mater. 2017, 3, pp. 1700057 (1 of 10).
Che, Yuchi et al—"Review of carbon nanotube nanoelectronics and macroelectronics"; 2014 IOP Publishing Ltd, Semicond. Sci. Technol. 29 (2014) 073001—(17pp).
Chen, Gugang et al "Enhanced gas sensing in pristine carbon nanotubes under continuous ultraviolet light illumination"; Scientific Reports | 2 : 343 | DOI: 10.1038/srep00343—pp. 1-7.
Chortos, Alex et al—"Universal Selective Dispersion of Semiconducting Carbon Nanotubes from Commercial Sources Using a Supramolecular Polymer"; ACSNano—ACS Nano 2017, 11, pp. 5660-5669.
De Volder, Michael F.L et al—"Carbon Nanotubes: Present and Future Commercial Applications"; www.sciencemag.org Science vol. 339 Feb. 1, 2013, pp. 535-540.
Ding, Jianfu et al—"Synthesis, characterization and photovoltaic applications of a low band gap polymer based on s-tetrazine and dithienosilole"; The Royal Society of Chemistry 2010; Chem. Commun., 2010, 46,pp. 8668-8670.
Ding, Jianfu et al—"The Preparation of 3,6-Bis(3-hexylthien-2-yl)-s-tetrazine and Its Conjugated Polymers"; Published online May 31, 2011 in Wiley Online Library (wileyonlinelibrary.com), wileyonlinelibrary.com/journal/jpola; pp. 3374-3386.
Ding, Jianfu et al—"Enrichment of large-diameter semiconducting SWCNTs by polyfluorene extraction for high network density thin film transistors"; The Royal Society of Chemistry 2014, Nanoscale, 2014, 6, pp. 2328-2339.
Ding, Jianfu et al—"A hybrid enrichment process combining conjugated polymer extraction and silica gel adsorption for high purity semiconducting single-walled carbon nanotubes (SWCNT)"; The Royal Society of Chemistry 2015, Nanoscale, 2015, 7, pp. 15741-15747.
Ellis, James E. et al—"Carbon Nanotube Based Gas Sensors toward Breath Analysis"; 2016 Wiley-VCH Verlag GmbH & Co. KGaA, Weinheim; ChemPlusChem 2016, 81, pp. 1248-1265.
Fennell, John F. Jr., et al—"Nanowire Chemical/Biological Sensors: Status and a Roadmap for the Future"; 2016 Wiley-VCH Verlag GmbH & Co. KGaA, Weinheim Angew. Chem. Int. Ed. 2016, 55, pp. 1266-1281.
Franklin, Aaron D.—"The road to carbon nanotube transistors"; 2013 Macmillan Publishers Limited, Jun. 27, 2013, vol. 498, Nature, pp. 443-444.
Fujigaya, Tsuyohiko et al—"Non-covalent polymer wrapping of carbon nanotubes and the role of wrapped polymers as functional dispersants"; IOP Publishing, Science and Technology of Advanced Materials; Sci. Technol. Adv. Mater. 16 (2015) 024802 (21pp).
Geier, Michael L. et al—"Controlled n-Type Doping of Carbon Nanotube Transistors by an Organorhodium Dimer"; ACS Publications; 2016 American Chemical Society; DOI: 10.1021/acs.nanolett. 6b01393, Nano Lett. 2016, 16, pp. 4329-4334.
Gomulya, W. et al—"Semiconducting Single-Walled Carbon Nanotubes on Demand by Polymer Wrapping"; 2013 Wiley-VCH Verlag GmbH & Co. KGaA, Weinheim, Adv. Mater. 2013, 25, pp. 2948-2956.
Homenick, Christa M. et al—"Fully Printed and Encapsulated SWCNT-Based Thin Film Transistors via a Combination of R2R Gravure and Inkjet Printing"; ACS Publications, American Chemical Society, ACS Appl. Mater. Interfaces 2016, 8, pp. 27900-27910.
Hu, Liangbing et al—"Carbon Nanotube Thin Films: Fabrication, Properties, and Applications"; 2010 American Chemical Society, Chemical Reviews, 2010, vol. 110, No. 10, pp. 5790-5844.
Ihly, Rachelle et al—"Tuning the driving force for exciton dissociation in single-walled carbon nanotube heterojunctions"; Nature Chemistry, vol. 8, Jun. 2016, pp. 603-609.
Ji, Qiyan, et al—"Photodegrading hexaazapentacene dispersant for surface-clean semiconducting single-walled carbon nanotubes"; 2016 Elsevier Ltd., Carbon 105 (2016) pp. 448-453.
Joo, Yongho el al—"Dose-Controlled, Floating Evaporative Self-assembly and Alignment of Semiconducting Carbon Nanotubes from Organic Solvents"; ACS Publications, 2014 American Chemical Society, Langmuir 2014, 30, pp. 3460-3466.
Joo, Yongho et al—"Isolation of Pristine Electronics Grade Semiconducting Carbon Nanotubes by Switching the Rigidity of the Wrapping Polymer Backbone on Demand"; 2015 American Chemical Society, ACS Nano, vol. 9, No. 10, pp. 10203-10213.
Khripin, Constantine Y. et al—"Spontaneous Partition of Carbon Nanotubes in Polymer-Modified Aqueous Phases"; JACS—Journal of The American Chemical Society, dx.doi.org/10.1021/ja402762e | J. Am. Chem. Soc. 2013, 135, pp. 6822-6825.
Kong, Jin et al—"Nanotube Molecular Wires as Chemical Sensors"; www.sciencemag.org, Science—Jan. 28, 2000 vol. 287, pp. 622-625.
Lefebvre, J. et al—"Carbon nanotube thin film transistors by droplet electrophoresis"; 2017; Elsevier Ltd., Materials Today Communications, vol. 10, pp. 72-79.
Lei, Ting et al—"Removable and Recyclable Conjugated Polymers for Highly Selective and High-Yield Dispersion and Release of Low-Cost Carbon Nanotubes"; ACS Publications, Journal of the American Chemical Society, J. Am. Chem. Soc. 2016, 138, pp. 802-805.
Lemasson, Fabien et al—"Debundling, selection and release of SWNTs using fluorene-based photocleavable polymers"; This journal is The Royal Society of Chemistry 2011, Chem. Commun., 2011, 47, pp. 7428-7430.
Li, Zhao et al—"Development of a New s-Tetrazine-Based Copolymer for Efficient Solar Cells"; JACS, American Chemical Society, J. Am. Chem. Soc. 2010, 132, pp. 13160-13161.
Li, Zhao et el—"Bisfuran-s-Tetrazine-Based Conjugated Polymers: Synthesis, Characterization, and Photovoltaic Properhes"; 2011 Wiley-VCH Verlag GmbH & Co., Macromol. Chem. Phys. 2011, 212, pp. 2260-2267.
Li, Zhao et al—"Alternating Copolymers of Dithienyl-s-Tetrazine and Cyclopentadithiophene for Organic Photovoltaic Applications"; ACS Publications; 2011 American Chemical Society, Chemistry of Materials, Chem. Mater. 2011, 23, pp. 1977-1984.
Li, Zhao et al—"Surface effects on network formation of conjugated polymer wrapped semiconducting single walled carbon nanotubes and thin film transistor performance"; 2015 Elsevier B.V., Organic Electronics 26 (2015) pp. 15-19.
Li, Zhao et al—"Raman microscopy mapping for the purity assessment of chirality enriched carbon nanotube networks in thinfilm transistors"; Tsinghua University Press; Springer, Nano Research 2015, 8(7): pp. 2179-2187.
Llanes-Pallas, Anna et al—"Modular Engineering of H-Bonded Supramolecular Polymers for Reversible Functionalization of Carbon Nanotubes"; JACS, ACS Publications; 2011 American Chemical Society, J. Am. Chem. Soc. 2011, 133, pp. 15412-15424.
Lobez, Jose M. et al—"Radiation Detection: Resistivity Responses in Functional Poly(Olefin Sulfone)/Carbon Nanotube Composites"; 2010 Wiley-VCH Verlag GmbH & Co., Radiation Sensors, Angew. Chem. Int. Ed. 2010, 49, pp. 95-98.
Lu, Fushen et al—"Separated Metallic and Semiconducting Single-Walled Carbon Nanotubes: Opportunities in Transparent Electrodes and Beyond"; ACS Publications, 2010 American Chemical Society, Langmuir 2011, 27, pp. 4339-4350.
Meyyappan, M.—"Carbon Nanotube-Based Chemical Sensors"; 2016 Wiley-VCH Verlag GmbH & Co., Chemical Sensors, small 2016, 12, No. 16, pp. 2118-2129.
Moser, Matthew L. et al—"Fast Electrochromic Device Based on Single-Walled Carbon Nanotube Thin Films"; ACS Publications, 2016 American Chemical Society, Nano Lett. 2016, 16, pp. 5386-5393.
Van Noorden, Richard—"The Trials of New Carbon"; 2011 Macmillan Publishers Limited, Nature, vol. 469, Jan. 6, 2011; pp. 14-16.
Norton-Baker, Brenna et al—"Polymer-Free Carbon Nanotube Thermoelectrics with Improved Charge Carrier Transport and Power Factor"; ACS Publications, 2016 American Chemical Society, ACS Energy Lett. 2016, 1, pp. 1212-1220.

(56) References Cited

OTHER PUBLICATIONS

Peng, Lian-Mao et al—"Carbon nanotube electronics: recent advances"; 2014 Elsevier Ltd., Materials Today, vol. 17, No. 9 Nov. 2014, pp. 433-442.

Pochorovski, Igor et al—"H-Bonded Supramolecular Polymer for the Selective Dispersion and Subsequent Release of Large-Diameter Semiconducting Single-Walled Carbon Nanotubes"; JACS, ACS Publications, 2015 American Chemical Society, J. Am. Chem. Soc. 2015, 137, pp. 4328-4331.

Qi, PengFei et al—"Toward Large Arrays of Multiplex Functionalized Carbon Nanotube Sensors for Highly Sensitive and Selective Molecular Detection"; 2003 American Chemical Society, Nano Lett., vol. 3, No. 3, 2003, pp. 347-351.

Raymor—"Ultra High-Purity Semiconducting SWNTs"—Technical Data Sheet; Nan Integris, 2016—7 pgs.

* cited by examiner

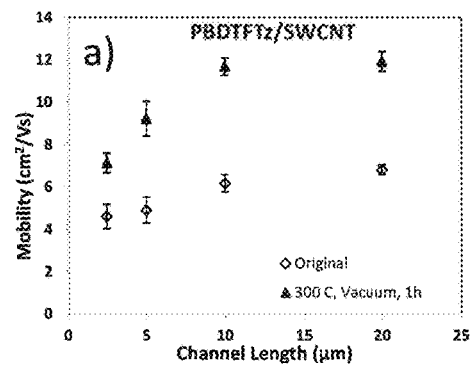
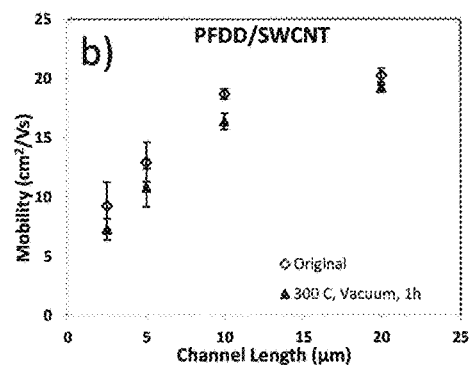
FIG. 8A  FIG. 8B
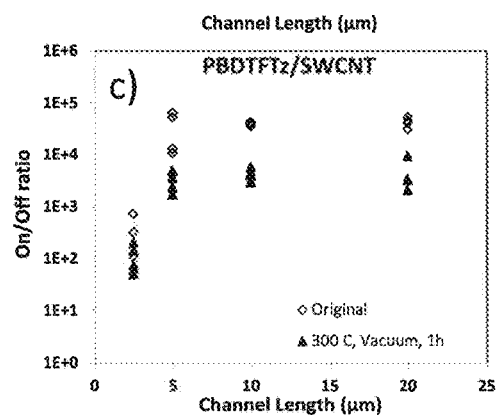
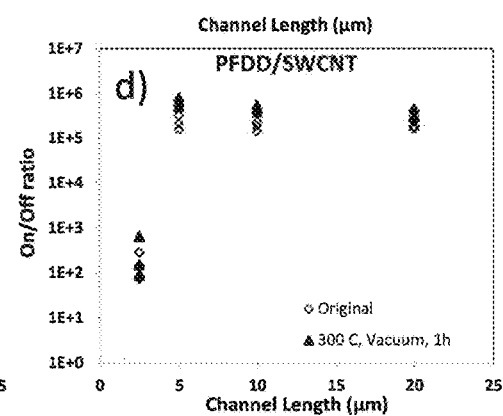
FIG. 8C  FIG. 8D
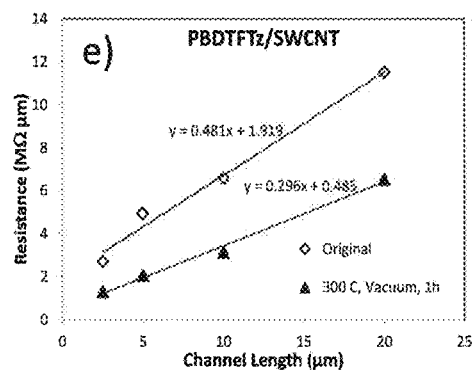
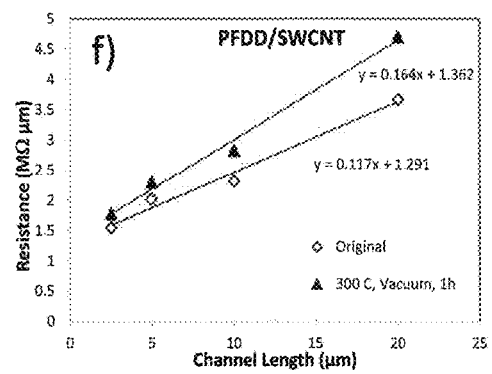
FIG. 8E  FIG. 8F

DECOMPOSABLE S-TETRAZINE BASED POLYMERS FOR SINGLE WALLED CARBON NANOTUBE APPLICATIONS

This is a Continuation-In-Part of U.S. application Ser. No. 15/401,421 filed on Jan. 9, 2017.

TECHNICAL FIELD

The present application relates to carbon nanotubes. In particular, it relates to the use of s-tetrazine based polymers for single walled carbon nanotube applications.

BACKGROUND

As new emerging materials, single-walled carbon nanotubes (SWCNTs) have recently attracted extensive research interest due to their specific electrical, optical and mechanical properties. For different applications, the raw SWCNT materials have to be purified and enriched, as they contain metallic (m) and semiconducting (sc) single-walled carbon nanotubes, amorphous carbon, catalyst and other impurities. For example, sc-SWCNTs can be used as the active channel materials in field effect transistors (FET) in logic circuit and other electrical devices. Among various purification methods, comparatively, polymer extraction (PE) approach is a low cost and scalable process, and the sc-SWCNTs materials from this process also show quite high purity level.

Recently, conjugated polymer extraction (CPE) processes have been developed to purify single walled carbon nanotube (SWCNT) raw materials. Compared with other surfactant-based methods, such as density gradient ultra-centrifugation (DGU), gel chromatography and biphasic separation, CPE is simple, scalable and cost effective, thus possessing properties that are highly desirable for industrial applications. More importantly, the dispersed product is obtained as an organic solvent-based dispersion with relatively high tube content (e.g. up to ~20%-50%). This leads to additional benefits in the application of SWCNT materials in device fabrication and performance.

However, one of the problems associated with the CPE process lies in the difficulty to remove conjugated polymer that remains on the sc-SWCNTs after purification or device fabrication. In other methods, surfactants are used to disperse tubes in solution. While these small molecules have a weaker interaction with sc-SWCNTs and can be easily removed from the sc-SWCNT surface by a simple rinsing step, a large excess of surfactant is required, which is undesirable in many circumstances. One advantage of the CPE process is that relatively low weight ratio (e. g. polymer/tube weight ratio <2) of polymeric dispersant is needed to form a stable dispersion, especially when conjugated polymers are used and/or at high concentration, when compared to small molecule surfactants that are present at a weight percentage of 95% or more.

Conjugated polymers have much stronger adhesion interactions with sc-SWCNTs, and can helically wrapped around the sc-SWCNTs. Furthermore, in non-polar organic media, the π-π stacking interaction between the conjugated polymer and the sc-SWCNT surface can be stronger than that in polar solvents. Even after thorough solvent rinsing, however, the polymer content in the dispersion can still be over ~50% by weight. This will reduce the sensitivity of a sensor using sc-SWCNTs in a chemiresistor or transistor.

One way to solve this problem is to use polymers with special chemical moieties that are introduced into the CPE process. These polymers can be metal-coordination polymers based on the interaction between ligand and metal ions, or H-bonded supramolecular polymers. These linkages can be easily broken by acid treatment such that the polymers will degrade into small units. Some polymers may contain degradable units, such as disilane, photocleavable o-nitrobenzylether and imine bonds. Other polymers may contain special units, such as azobenzene or foldable oligomers, so the conformation of these polymers can be changed by external stimuli, such as thermal isomerization or by using different solvents.

Although the aforementioned degradable polymers can be used for sc-SWCNT purification and/or dispersion, there are still some major drawbacks. For example, the polymer can only be partially removed after degradation; most of the degradations are carried out in solution; after polymer degradation, the sc-SWCNT will form bundles in solution which cannot be easily used for device fabrication; and none of the above polymer degradation was demonstrated on device surfaces after fabrication with the expectation that the sc-SWCNT would be likely removed from the surface.

Thus, there is a need for polymers that form stable sc-SWCNT dispersions, which can be easily removed from the sc-SWCNTs either in solution or post-device fabrication without removal of the sc-SWCNTs from the surface of the device.

The following documents (all of which are hereby incorporated by reference) disclose other classes of degradable and/or removable polymers for use in CPE processes for purifying CNT:

Pochorovski I, et al. *J. Am. Chem. Soc.* 2015, 137, 4328-4331.
Toshimitsu F, et al. *Nature Communications.* 5:5041, 9 pages.
Umeyama T, et al. *Chem. Commun.*, 2010, 46, 5969-5971.
Lei T, et al. *J. Am. Chem. Soc.* 2016, 138, 802-805.
Lemasson F, et al. *Chem. Commun.*, 2011, 47, 7428-7430.
Wang H, et al. *Nano Today*, (2015) 10, 737-758

A few of the polymers disclosed in these documents comprise heterocyclic N-containing rings, but none disclose tetrazine-based polymers.

In addition, US 2008/287638 and US 2013/0253120 (both of which are incorporated by reference) disclose classes of conjugated polymers that may contain a tetrazine group that associate with carbon nanotubes.

In particular, US 2013/0253120 discloses polyolefins, which may be tetrazine functionalized polyolefins, for modifying nanoparticles (including CNTs). However, this document does not disclose the class of s-tetrazine polymers for use in CPE extractions, nor does it disclose the degradability of these polymers.

US 2008/287638 discloses a class of "sticky" supramolecular polymers comprising a conjugated or electroactive segment (e.g. fluorenyl) and a "sticky" segment that non-covalently binds with the sidewall of the CNT, the sticky segment possibly comprising a tetrazine. However, this document does not disclose the particular class of s-tetrazine polymers, let alone any particular polymers comprising a tetrazine. Nor does it disclose the use of these polymers for purifying sc-SWCNTs in a CPE process. Furthermore, there is no discussion of the degradability of the polymers.

It is also known that tetrazines react with CNTs to form covalent bonds thereby breaking C=C bonds in the CNT framework. For example, Broza G. *Chemistry & Chemical Technology*, Vol. 4, No. 1 (2010), 35-45, discloses that tetrazines are known to form covalent bonds thereby breaking C=C bonds in the CNT framework.

U.S. Pat. No. 8,673,183; Li Z, et al. *J. Am. Chem. Soc.* 2010, 132, 13160-13161; and Li Z, et al. *Macromol. Chem. Phys.* 2011, 212, 2260-2267 (all of which are incorporated by reference), all disclose the class of s-tetrazine polymers for use in electronic devices, but not for use in association with carbon nanotubes (CNTs) and especially not for use in a CPE process to purify CNTs.

One area of device fabrication utilizing nanotubes is chemical sensors. Ellis et al (*ChemPlusChem*, 2016, 81, 1248-1265) provide a review of synthetic methods used to functionalize CNT-based gas sensors, specifically those sensors that target biologically relevant breath markers.

In addition, J. F. Fennell, Jr. et al (*Angew. Chem. Int. Ed.* 2016, 55, 1266-1281) discuss the use of nanowires (NWs) in chemosensor development.

T. Zhang et al (Nanotechnology 19 (2008) 332001 (14 pp)) review progress on the development of different types of carbon nanotube (CNT)-based nanosensors, with focus placed on the means used to improve the sensing performance (sensitivity, selectivity and response time) through the rational functionalization of CNTs with different methods (covalent and non-covalent) and with different materials (polymers and metals).

M. Meyyappan (small, 2016, 12, No. 16, 2118-2129) reviews the use of carbon nanotubes in gas and vapor sensing.

Although it is broadly disclosed that conjugated polymers that may contain a tetrazine group can associate with carbon nanotubes, it is also known that tetrazines can react with CNT to form covalent bonds, and none of the prior art contains examples of polymers containing a tetrazine group where the polymer associates with CNT.

Therefore it would not necessarily be expected that tetrazine polymers would associate with rather than react with CNT. In addition, there is no indication in the art that tetrazine-containing polymers would be useful in a CPE process for purifying CNTs, let alone the specific class of polymers of s-tetrazine polymers.

It has now been found that s-tetrazine based polymers can be used for sc-SWCNT purification, dispersion and device fabrication. Since s-tetrazine units can be easily decomposed by photo irradiation or thermal treatment, both in solution or on the device surface, the small molecules formed by decomposition can be washed away in solution or evaporated by laser irradiation or under vacuum in the solid state. This enables higher sensitivity sensors for gases, such as ammonia or nitrogen dioxide ($NO_2$).

SUMMARY

Decomposable s-tetrazine based polymers for single walled carbon nanotube applications in their general forms will first be described, and then their implementation in terms of embodiments will be detailed hereafter. These embodiments are intended to demonstrate a process for producing a chemical sensor that detects one or more chemicals in the ppt to ppb range; a chemical sensor comprising a network of semiconducting single-walled carbon nanotubes (sc-SWCNTs) that that detects one or more chemicals in the ppt to ppb range; and a chemical sensor for detection of gaseous ammonia or gaseous nitrogen dioxide in the ppt to ppb range, the sensor comprising a network of semiconducting single-walled carbon nanotubes (sc-SWCNTs). Decomposable s-tetrazine based polymers for single walled carbon nanotube applications will then be further described, and defined, in each of the individual claims which conclude this specification.

In one aspect of the present invention, there is provided a chemical sensor for detection of one or more chemicals in the ppt to ppb range, the sensor made by a process comprising the steps of: applying a dispersion of a sc-SWCNT/s-tetrazine based conjugated polymer composite to a substrate; applying heat and/or UV light to decompose the s-tetrazine based conjugated polymer; and removing the resulting decomposition products.

In a further aspect of the present invention, there is provided a process for producing a chemical sensor that detects one or more chemicals in the ppt to ppb range, the process comprising: applying a dispersion of a sc-SWCNT/s-tetrazine based conjugated polymer composite to a substrate; applying heat and/or UV light to decompose the s-tetrazine based conjugated polymer; and removing the resulting decomposition products.

The above sensor may have a lower detection limit of from 4 ppt to 100 ppb, or from 3 ppt to 1 ppb. In addition, the sensor can detect one or more chemicals in a gaseous or liquid phase; the one or more chemicals may be gaseous ammonia or gaseous nitrogen dioxide ($NO_2$). It is also possible for the sensor to detect one or more chemicals in the ppb to ppm range, in which case the sensor may have a lower detection limit of from 4 ppb to 100 ppm, or from 3 ppb to 1 ppm.

The s-tetrazine based polymer may have the following structure:

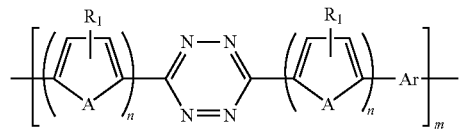

where A is O, S, Se or C=C; n is an integer from 1 to 4; R1 is independently H, F, CN or a C1-C20 linear or branched aliphatic group; Ar is one or more substituted or unsubstituted aromatic units; and, m is an integer 5 or greater.

Examples of the s-tetrazine based polymer include (but are not limited to): PBDTFTz:

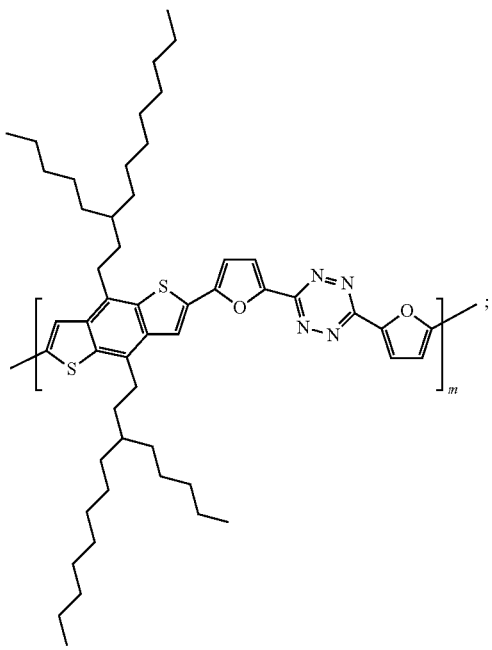

PDTSTTz:

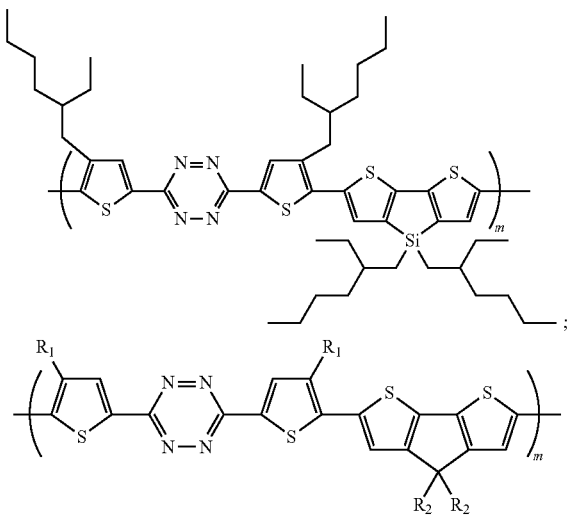

where $R_1$ and $R_2$=2-ethylhexyl; or $R_1$=2-ethylhexyl and $R_2$=hexyl; or $R_1$=hexyl and $R_2$=2-ethylhexyl; or $R_1$ and $R_2$=hexyl; or $R_1$=methyl and $R_2$=2-ethylhexyl;
or PCPDTFTz:

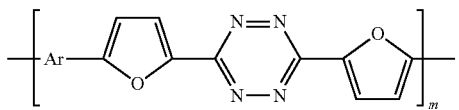

in which Ar=cyclopenta[2,1-b;3.4-b]dithiophene

The decomposition products may be removed by rinsing, evaporation, sublimation or any combination thereof.

In addition, the conjugated polymer may comprise a polyfluorene or a polythiophene. In addition, the conjugated polymer may comprise a 3-alkyl-substituted polythiophene; a 9,9-diC10-36-alkyl-substituted polyfluorene; a 9,9-diC10-18-alkyl-substituted polyfluorene; a 3-C10-18-alkyl-substituted polythiophene; a copolymer of 9,9-diC10-18-alkyl-substituted fluorene with one or more co-monomer units, the co-monomer comprising one or more of thiophene, bithiophene, phenylene, bipyridine, carbazole, anthracene, naphthalene or benzothiadiazole; a copolymer of 3-C10-18-alkyl-substituted thiophene with one or more co-monomer units, the co-monomer comprising one or more of fluorene, bithiophene, phenylene, bipyridine, carbazole, anthracene, naphthalene or benzothiadiazole. An example of a conjugated polymer that may be used in the process is poly(9,9-di-n-dodecylfluorene) (PFDD).

In the process, the weight ratio of the conjugated polymer to the sc-SWCNTs can have a maximum value of 5, or a maximum value of 2, and may be in the range between 1 and 5. Furthermore, the weight ratio of the s-tetrazine based polymer to the sc-SWCNTs can have a maximum value of 8, or a maximum value of 8, or a maximum value of 4, and may be in the range between 1 and 4.

In yet another aspect of the present invention, there is provided chemical sensor for detection of gaseous ammonia or gaseous nitrogen dioxide in the ppt to ppb range, the sensor comprising a network of semiconducting single-walled carbon nanotubes (sc-SWCNTs).

The aforementioned chemical sensor may have a lower detection limit of from 4 ppt to 100 ppb, or from 3 ppt to 1 ppb. Furthermore, the sensor may have a lower detection limit of from 4 ppb to 100 ppm, or from 3 ppb to 1 ppm. It is also possible for the sensor to detect gaseous ammonia or gaseous nitrogen dioxide in the ppb to ppm range, in which case the sensor may have a lower detection limit of from 4 ppb to 100 ppm, or from 3 ppb to 1 ppm.

Wherever ranges of values are referenced within this specification, sub-ranges therein are intended to be included, unless otherwise indicated. Where characteristics are attributed to one or another variant of: the process of purifying sc-SWCNTs with s-tetrazine based polymers; the use of s-tetrazine based polymers for purification of sc-SWCNTs; and the method for producing thin film transistors using s-tetrazine based polymers, unless otherwise indicated, such characteristics are intended to apply to all other variants where such characteristics are appropriate or compatible with such other variants.

Further features will be described or will become apparent in the course of the following detailed description.

BRIEF DESCRIPTION OF DRAWINGS

For clearer understanding, preferred embodiments will now be described in detail by way of example, with reference to the accompanying drawings, in which:

FIGS. 8a-8f illustrate a comparison of properties at various channel lengths, between TFTs prepared with PBDTFTz/SWCNT (a, c and, e) or PFDD/SWCNT (b, d and f) dispersions.

DETAILED DESCRIPTION OF PREFERRED EMBODIMENTS

The following s-tetrazine based polymers can be used for SWCNT purification, dispersion and device fabrication:

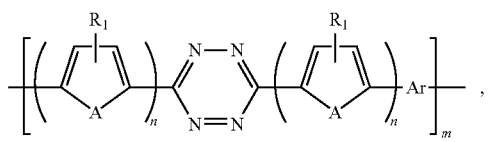

where each A is O, S, Se or C≡C; each n is an integer from 1 to 4; each R1 is independently H, F, CN or a C1-C20 linear or branched aliphatic group; Ar is one or more substituted or unsubstituted aromatic units; and, m is an integer 5 or greater.

Examples of s-tetrazine based polymers include poly[2,6-(4,4'-bis(2-ethylhexyl)dithieno[3,2-b:2',3'-d]silole)-alt-5,5'-(3,6-bis[4-(2-ethylhexyl)thienyl-2-yl]-s-tetrazine)], also identified with the acronym PDTSTTz:

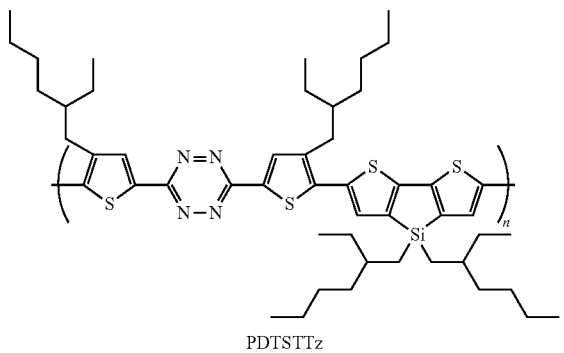

PDTSTTz

The synthesis, characterization and photovltaic applications of PDTSTTz are disclosed by J. Ding et al. in *Chem. Commun.*, 2010, 45, 8668-8670, the contents of which are incorporated herein by reference.

Another class of s-tetrazine based polymers include the following five, which are disclosed by Z. Li et al. iin *Chem. Mater.* 2011, 23, 1977-1984, the contents of which are incorporate herein by reference:

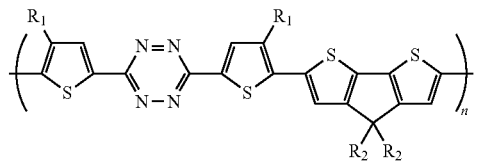

P1: $R_1$ = 2-ethylhexyl, $R_2$ = 2-ethylhexyl
P2: $R_1$ = 2-ethylhexyl, $R_2$ = hexyl
P3: $R_1$ = hexyl, $R_2$ = 2-ethylhexyl
P4: $R_1$ = hexyl, $R_2$ = hexyl
P5: $R_1$ = methyl, $R_2$ = 2-ethylhexyl In particular, P4, also known as PCPDTTTz, is used in the production of efficient solar cells, as disclosed by Z. Li et al. in *J. Am. Chem. Soc.*, 2010, 132, 13160-13161, the contents of which are incorporate herein by reference.

Another example includes PCPDTFTz, the synthesis, characterization and photovoltaic properties of which are disclosed by Z. Li et al. in *Macromol. Chem. Phys.* 2011, 212, 2260-2267, the contents of which are incorporate herein by reference:

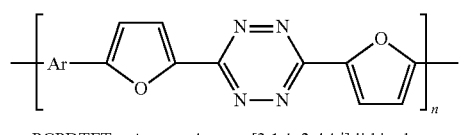

PCPDTFTz: Ar = cyclopenta[2,1-b;3.4-b']dithiophene

In one embodiment, the following s-tetrazine based polymer (PBDTFTz), which contains alternating bisfuran-s-tetrazine and benzo [1,2-b:4,b-b']dithiophene units, can be used for SWCNT purification, dispersion and device fabrication:

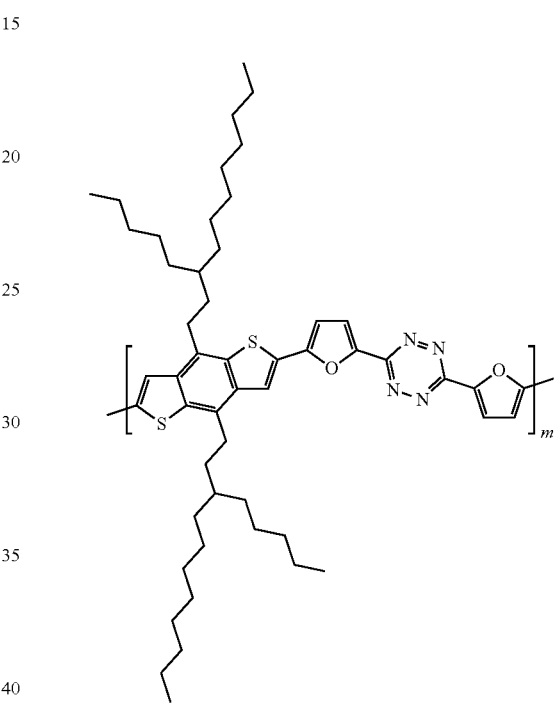

Decomposition of s-Tetrazine Based Polymers

Differential scanning calorimetry (DSC) curves demonstrate that s-tetrazine polymer can be decomposed thermally at around 250° C.

Figure 1:
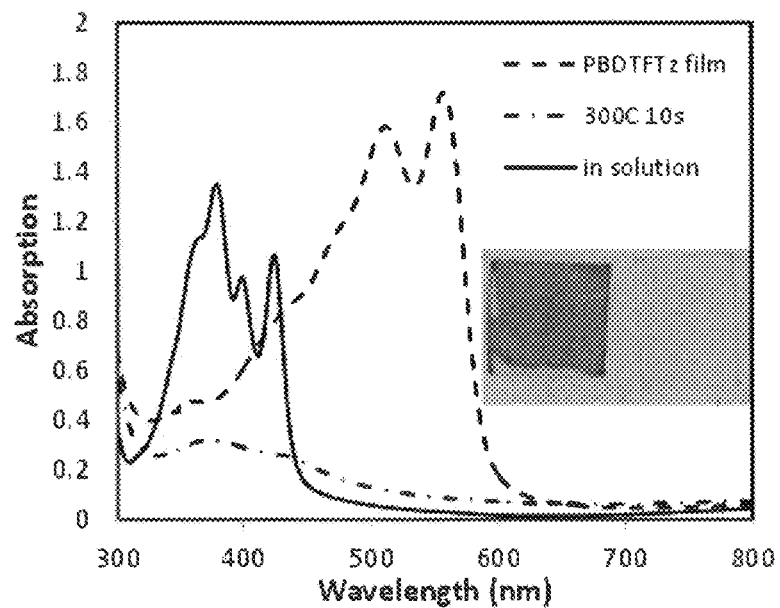
FIG. 1 illustrates UV absorption spectra of PBDTFTz film on glass slides before and after being heated at 300° C. for 10 s. Inset shows the pictures of the solution or film before (left) and after (right) decomposition.

This is illustrated in FIG. 1, in which a PBDTFTz film on a glass slide was heated at 300° C. for 10 s. The polymer PBDTFTz was synthesized as disclosed by Z. Li et al., *Macromol. Chem. Phys.*, 2011, 212, 2260. Broad UV absorption bands at 511 nm and 552 nm decrease with the appearance of new peaks around 380 nm, following thermal degradation. The solid line shows the UV spectra of the product after thermal decomposition in toluene solution. Inset shows the pictures of the solution or film before (left) and after (right) decomposition, in which the purple color of the initial polymer film/solution decays to yellow. GPC analysis of the decomposed product from thermal degradation confirms a dramatically decreased molecular weight.

The product contains 90% of dicyano compound (1): It has much shorter conjugation length than PBDTFTz so the absorption spectrum is blue shifted and contains well-resolved peaks. The decomposition scheme is shown as follows:

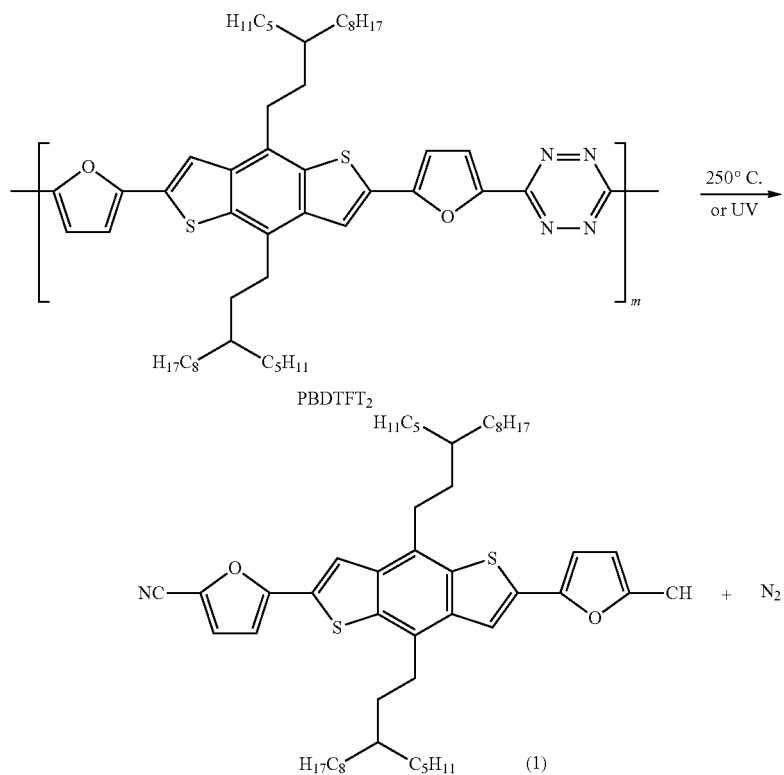

Figure 2:
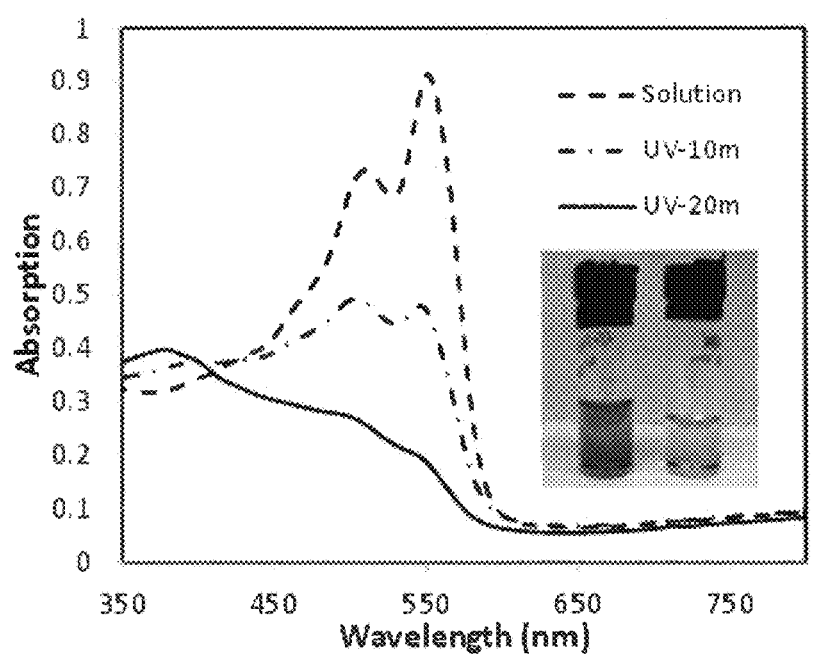
FIG. 2 illustrates UV absorption spectra of PBDTFTz in toluene solution before and after irradiated with UV light for 10 or 20 min.

Furthermore, s-tetrazine polymer is sensitive to strong UV light. This is illustrated in FIG. 2, in which the broad absorption bands at 511 nm and 552 nm decrease after a solution of PBDTFTz in toluene solution is irradiated with UV light for 10 or 20 min. As with thermal decomposition, the purple color of the initial polymer solution decays to yellow. GPC analysis of the decomposed product from photolytic degradation confirms that the degradation product is primarily 90% of dicyano compound (1) shown above.

Displacement of PFDD with s-Tetrazine Based Polymers

The interaction between s-tetrazine based polymers and SWCNT is quite strong, but not strong enough to disrupt the SWCNT structure. Other polymers, such as those of the polyfluorene class (PFDD), can be easily displaced by treating the PFDD dispersion with s-tetrazine polymer solution.

In one embodiment, a simple polymer exchange process can be used to replace poly(9,9-di-n-dodecylfluorene) (PFDD) on SWCNTs with PBDTFTz by a simple polymer exchange.

The polymer PBDTFTz was synthesized as disclosed in Z. Li et al., *Macromol. Chem. Phys.*, 2011, 212, 2260. High purity PFDD/sc-SWCNT solution was prepared as disclosed by Ding, Z et al. Nanoscale, 2014, 6, 2328, with a polymer/tube ratio of 1.3 and tube concentration at 165 mg/L. A PBDTFTz solution (1 g at 0.87 mg/mL) and toluene (3 g) was added to above solution (1 g), and the mixture was bath sonicated for 30 min. Then the solution was filtered on a Teflon membrane with pore size of 200 nm and washed with toluene (10 mL). The filter cake was then dispersed in toluene (4 g) and labeled as the product after first exchange. This process was repeated to obtain the product from a second polymer exchange. The polymer/tube ratio and solution concentration can be easily adjusted by filtration, dilution or addition of polymer. The final PBDTFTz/SWCNT dispersion has tube concentration at 25.5 mg/L and polymer/tube ratio at 4/1. A similar PFDD/SWCNT dispersion was also prepared.

Figure 3:
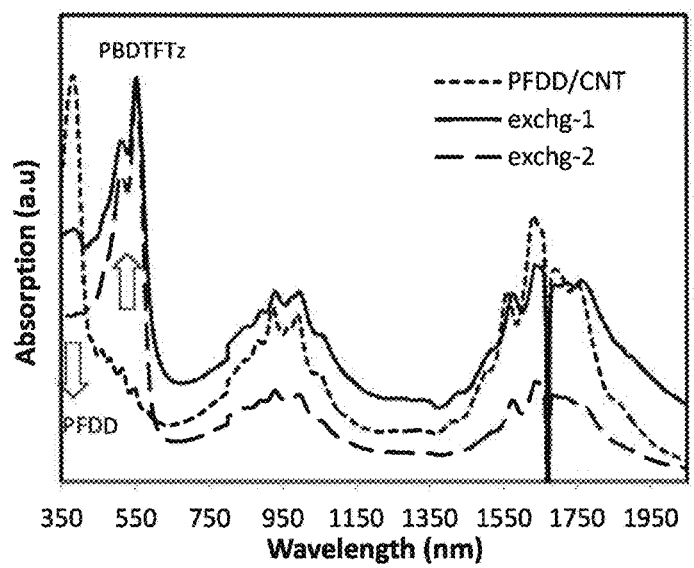
FIG. 3 illustrates UV absorption spectra of polymer/SWCNT dispersions in toluene of an original PFDD/SWCNT dispersion followed by polymer exchanges with PBDTFTz.

FIG. 3 illustrates a UV absorption spectra of the aforementioned polymer/SWCNT dispersions in toluene: original PFDD/SWCNT (dotted line), after 1st (solid line) and 2nd (dashed line) polymer exchange with PBDTFTz. In the first exchange, after bath sonication, filtration and rinsing, more than half of PFDD on the SWCNT surface was replaced by PBDTFTz. After the second ligand exchange, the PFDD peak at 380 nm in the UV spectra totally disappeared, indicating the complete replacement of PFDD by PBDTFTz, whose absorption peaks are located at 511 and 552 nm. In the meantime, the shape and resolution of S11 (1500 to 1900 nm) and S22 (700-1100 nm) bands of the SWCNTs stay untouched, indicating the formation of a stable PBDTFTz/SWCNT dispersion. It was also found that the ratio of PBDTFTz/SWCNT can be reduced to ~2.6/1 in the dispersion even after thorough dilution and rinsing step, agreeing well with the stronger interaction of PBDTFTz with SWCNTs than that of PFDD, whose ratio to SWCNT can be reduced to ~1.2/1 under similar condition.

Clean SWCNT Networks

As discussed above, s-tetrazine based polymers can be decomposed by photo irradiation or heating. After decomposition, the resulting small molecules can be washed away in solution or evaporated under laser irradiation or heating under vacuum if it is in the solid state. In this manner, clean SWCNT networks can be obtained, which is desirable for electrical devices application, such as thin film transistors (TFTs) or sensors. This is discussed further below in reference to FIG. 4.

Use of PBDTFTz/SWCNT Dispersions for Preparation of TFT

PBDTFTz/SWCNT dispersions can be used to prepare electronic devices.

Figure 4:
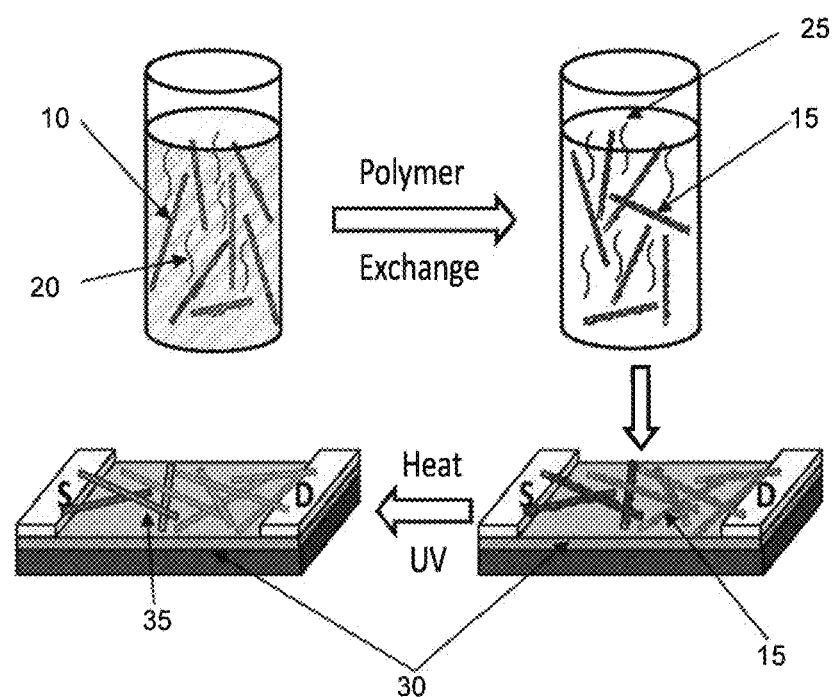
FIG. 4 illustrates the application of decomposable s-tetrazine based polymer for preparation of SWCNT thin film transistors with enhanced contact.

The use of decomposable s-tetrazine based polymer for producing SWCNT thin film transistors with enhanced contact, is summarized in FIG. 4. A dispersion of PFDD (20) and PFDD/SWCNT (10) undergoes a polymer exchange in which an s-tetrazine based polymer (25) displaces the PFDD, resulting in an associated complex of s-tetrazine/SWCNTs (15). Once the PFDD (20) is removed, the resulting dispersion is then applied to a substrate (30). Following the application of heat and/or UV light, the s-tetrazine based polymer decomposes, with the resulting decomposition products removed, leaving behind clean SWCNT networks (35).

In-situ transistor characterization under laser reveals the decomposition of PBDTFTz and evaporation of the small molecule compounds formed. Further investigation of the resistance from different channel length devices demonstrates dramatically improved contact between tubes due to removal of wrapping polymers. This fully exposed tube network can be particularly attractive for sensor applications, and results in improved contact.

TFT devices were fabricated using prefabricated devices with a 230 nm thick thermal oxide layer. The chip has pre-patterned Au electrodes with 4×4 TFT devices at channel lengths of 20, 10, 5, 2.5 µm and a channel width of 2,000 µm respectively. The chip was soaked in a 5% Hellmanex solution for 20 min at 60° C. before rinsed with water and isopropanol, blow-dried with nitrogen. The polymer/tube dispersion (0.1 mL) was then spread on the chip surface and the chip was soaked for 10 min under toluene vapor. The chip was then rinsed with toluene (5 mL) and blow dried with nitrogen before annealed at 140° C. for 10 min in air.

As an example, the PBDTFTz/SWCNT dispersion prepared above was used to prepare thin film transistors (TFT) on a freshly cleaned and pre-patterned $SiO_2$ substrate according a procedure disclosed by Z. Li, J. Ding et al., in Org. Electron. 2015, 26, 15. The resulting TFT devices have a bottom contact and common bottom gate configuration. For comparison, devices prepared from a PFDD/SWCNT dispersion were also fabricated at the same concentration and polymer/tube ratio.

Figure 5:
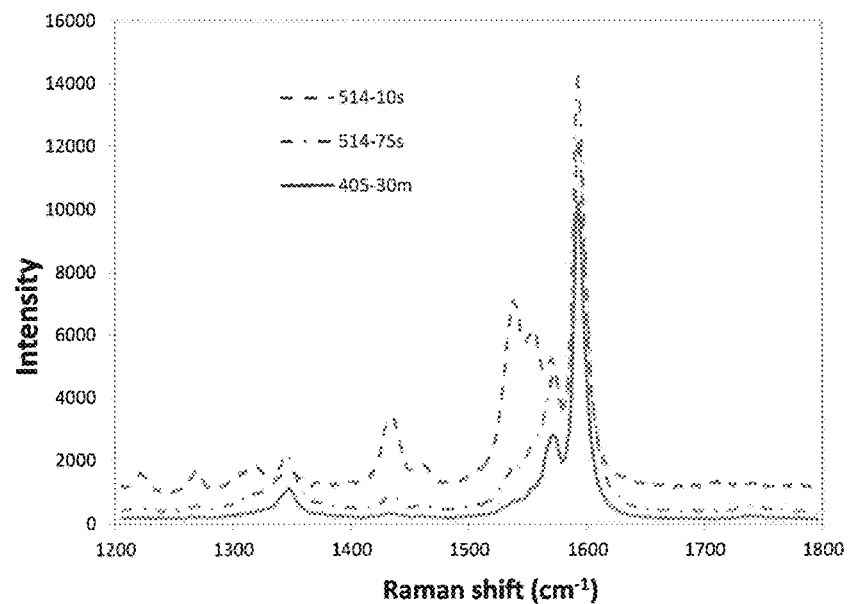
FIG. 5 illustrates Raman spectra of a PBDTFTz/SWCNT film on a silicon substrate during laser irradiation.

The degradation of the PBDTFTz on the SWCNT network was monitored by resonance Raman spectroscopy as shown in FIG. 5. Under 514 nm laser irradiation, the intensities of Raman shift at 1430 and 1530 $cm^{-1}$ from PBDTFTz gradually decreased, while the D and G bands from SWCNTs began to dominate. After 30 minutes exposure of the network to a 405 nm laser, all of the signals from PBDTFTz disappeared and only a clean spectrum of the SWCNTs remained.

Figure 6:
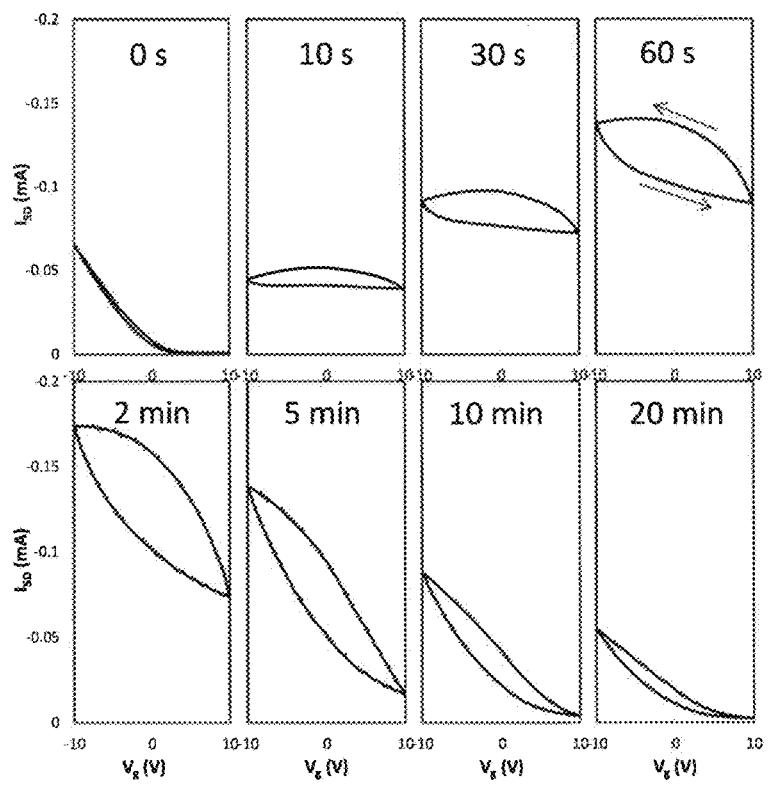
FIG. 6 illustrates the transfer curve of TFTs from a PBDTFTz/SWCNT dispersion at different irradiation time under 405 nm laser.

The TFT transistor was also characterized simultaneously under 405 nm laser irradiation. FIG. 6 illustrates the transfer curve of TFTs from a PBDTFTz/SWCNT dispersion at different irradiation time under 405 nm laser. $V_{SD}$=1V and active channel length and width are 20 and 2000 µm respectively. Arrows show the sweeping direction.

In the first 2 min, the on-current (at $V_g$=−10V) of the TFT increased gradually from 70 to 170 µA while the off-current at $V_g$=10V increased more dramatically by several orders of magnitude, which resulted to very poor on/off ratio. The hysteresis of the transfer curve also became more severe. However, this change reached plateau at 2 min and then slowly moved back.

This phenomenon can be explained by the degradation of PBDTFTz. Under 405 nm laser irradiation, PBDTFTz begins to decompose with the formation of dicyano (compound (1)) and release of nitrogen gas according to the decomposition scheme above. Compound (1) contains two cyano groups in each molecule and is a very strong p-doping agent for SWCNT. During PBDTFTz degradation, compound (1) that is formed will adhere on tubes first, and this will cause more p-doping effect (in addition to oxygen from the air) and shift the threshold voltage towards a positive direction. Longer time laser irradiation will further evaporate compound (1) that is formed and this p-doping effect will then alleviate.

Since the resulting TFTs always show a low on/off ratio, this suggests that compound (1) may not be completely removed from tube surface by simple laser irradiation. However, this decomposition reaction can be accelerated at a higher temperature; compound (1) can be completely removed at 300° C. under vacuum. The TFTs from PFDD/SWCNT was also characterized under laser irradiation, only slightly decreasing of on-current was observed, which can be attributed to the decreased p-doping of $O_2$ under laser light as all measurements were carried out in ambient conditions.

Comparison of Networks Based on PFDD/SWCNT and PBDTFTz/SWCNT

Figure 7A:
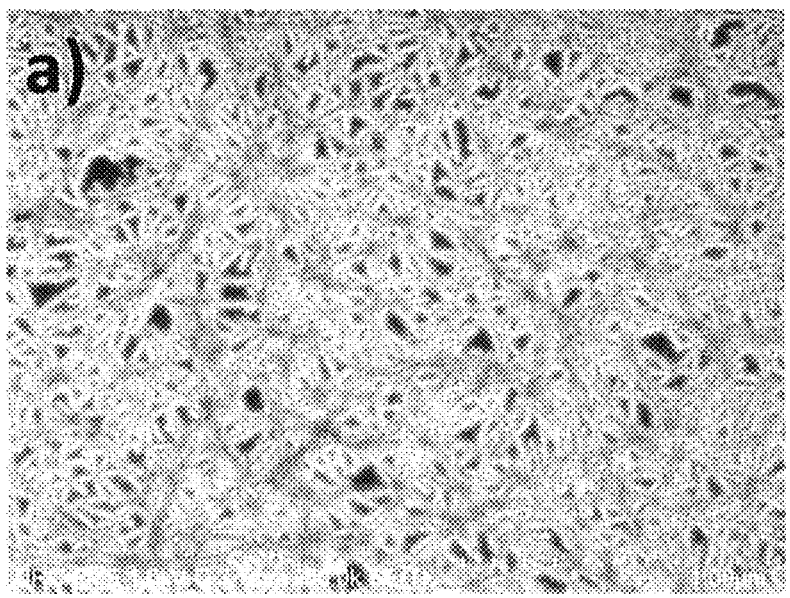
FIGS. 7a and 7b are SEM images of the tube network on $SiO_2$ substrate prepared from polymer (a) PBDTFTz/SWCNT and (b) PFDD/SWCNT dispersion.
Figure 7B:
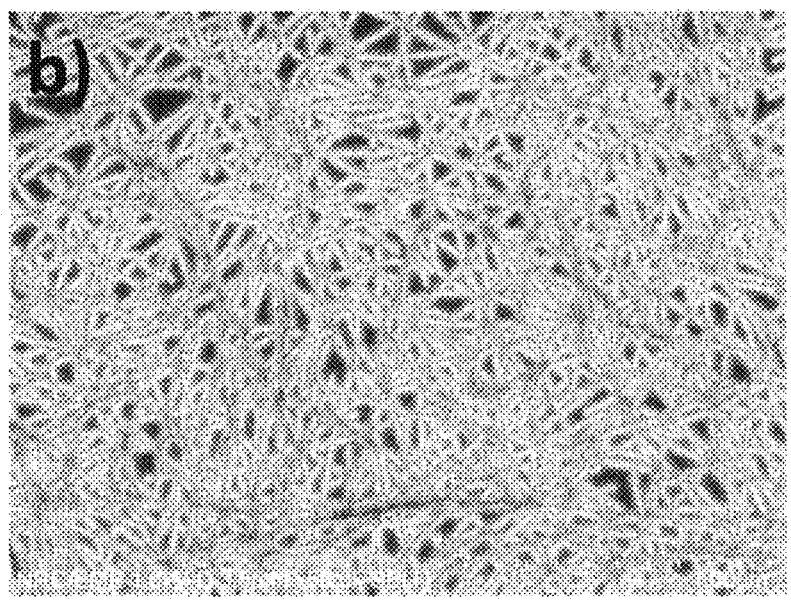

In general, the TFTs from PFDD/SWCNT have higher current and mobility, although their SEM images show quite similar tube density to those of PBDTFTz/SWCNT (see FIGS. 7a and 7b). The weight ratio of polymer/SWCNT is 4:1, while the concentration of SWCNT is 25.5 mg/L. The scale bar on the right bottom corner of the image is 1 µm.

Further examination reveals a higher degree of bundles and curved tube conformation in the PBDTFTz/SWCNT network, which may limit the contact between tubes.

FIGS. 8a-8f illustrate a comparison of properties at various channel lengths, between TFTs prepared with PBDTFTz/SWCNT (a, c and, e) or PFDD/SWCNT (b, d and f) dispersions. In particular, FIGS. 8(a) and (b) measure mobility; 8(c) and (d) measure On/off ratio; and 8(e) and (f) measure resistance of TFTs prepared from PBDTFTz/SWCNT (a, c, e) or PFDD/SWCNT (b, d, f) dispersions at various channel length. The channel width is 2,000 µm. Polymer/tube weight ratios are 4/1 and concentration of SWCNT is 25.5 mg/L.

More detailed characterization of the TFTs with different channel length from PBDTFTz/SWCNT before, and after, decomposition is shown in FIG. 8. For PBDTFTz/SWCNT TFTs, after removal of PBDTFTz, the mobility almost doubled due to better contact between tubes, whereas the mobility from PFDD/SWCNT slightly decreased due to decreased p-doping level (from $O_2$ and moisture) after heating and vacuum treatment. The on/off ratio of PBDTFTz/SWCNT TFTs decreased slightly after decomposition due to the raised off-current. The sheet resistance ($R_\square$ and contact resistance ($R_c$) could be extracted from the data of the devices with various channel length.

For PBDTFTz/SWCNT TFTs, after degradation, $R_\square$ decreased from 0.481 to 0.296 MΩ while $R_c$ decreased more dramatically from 0.960 to 0.242 KΩ µm. It is interesting that the removal of insulating polymer layer on tubes has more effect on $R_c$ than $R_\square$. This also demonstrates the significance of removal of the insulation polymer layer on the tube surface within a network.

For PFDD/SWCNT TFTs, after similar treatment, on the contrary, $R_\square$ increased from 0.117 to 0.164 MΩ, while $R_c$ remained almost unchanged, which can be attributed to decreased p-doping level after vacuum and thermal treatment.

The complete and easy removal of dispersant from the tube surface not only improves the device performance of transistors, but also benefits the sensitivity of the devices. This kind of wholly exposed tube surfaces is highly desired for sensor applications.

In the aforementioned TFT device characterization: I-V curves were collected on a probe station at ambient condition and the mobility was calculated from the $I_{sd}$-$V_g$ transfer curve in the linear regime based on a parallel plate model. Due to high channel width/length ratio (≥100), the contribution arising from tubes outside the defined channel area can be ignored. For TFT testing under laser irradiation, a 405 nm LDCU laser control unit was used and the laser beam was reflected onto the active channel as shown in FIG. 5.

Raman spectra were acquired with an InVia Raman microscope (Renishaw) on finished devices, using 514 nm laser excitation source and 100 magnification objective lens. SEM images were obtained using Hitachi SU-5000 operated at 1 kV (charge contrast imaging mode on $SiO_2$/Si substrate). UV absorption spectra were collected on a UV-Vis NIR spectrophotometer (Cary 5000, Varian) over a wavelength range from 300 to 2100 nm.

For the sensor tests, the polymer/SWCNT networks on chips were put into a chamber (volume ~20 mL) mounted with an Ossila chip and circuit board. The device channel length and width were 30 μm and 1 mm, respectively. The concentration of input ammonia gas was controlled with two mass flow controllers: one with a constant flow of 1 slm dry air/nitrogen and the other with 10 second pulse of 10, 20, 40, 80 and 160 sccm of 5 ppm ammonia in nitrogen.

Chemical Sensors Based on Sc-SWCNT Networks

Although the removal of polymer leads to a modest gain in transistor performance, the exposed nanotube surfaces provide a desirable platform for several applications, including chemical sensing of molecules. The novel chemistry described herein and its ability to yield bare high purity sc-SWCNT thin films can enable the optimized performance of a variety of devices, especially: high performance transistors based on aligned SWCNT, photovoltaic, and optoelectronic devices and foremost, sensors that are capable of ppb sensing, which can be applied to both environmental and health monitoring applications.

As an example, sc-SWCNT networks demonstrated rapid and reversible responses in ammonia ($NH_3$) sensing experiments, while the unwrapped nanotube networks proving superior in terms of signal to noise ratio and a detection limit calculated to be 2.5 ppb, almost four times better than polymer wrapped nanotubes.

sc-SWCNT network transistors were tested as sensors for ammonia using gas pulses. It was found that under continuous exposure, the transistor sensitivity is so pronoucned that complete current suppression was observed, and recovery occurred upon exposure to ambient air. With a pulse experiment, a reversible response is observed under dry air flow.

These devices were first tested as chemiresistors. Severe current drift was often found, mainly attributable to water/$O_2$ redox process at the $SiO_2$/nanotube/air interface, which may related to the initial doping state of the SWCNT materials due to uncontrollable variations in the process history during device fabrication. The transistor configuration, with the gate voltage as a tuning knob, permits a path towards finding the best operation condition and minimize baseline drifts. In these experiments, transistors were also heated to 96° C. to accelerate the release of adsorbed $NH_3$.

Figure 9:
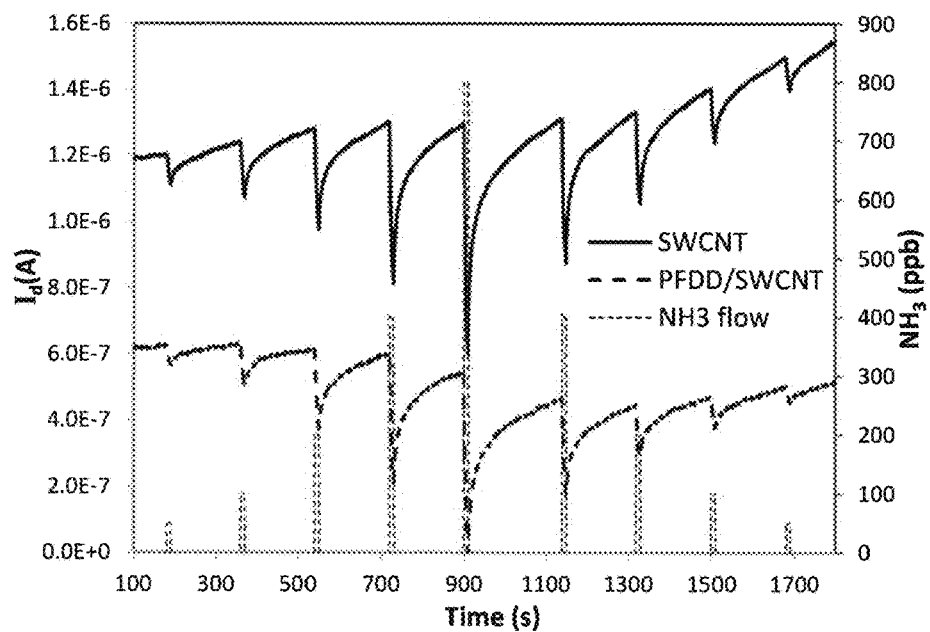
FIG. 9. illustrates a transistor response to NH3 gas for PBDTFTz/SWCNT (after polymer decomposition) and PFDD/SWCNT network, monitored by the Source/Drain current versus time following a series of NH3 gas pulses.

FIG. 9 shows the response of source/drain current to 10 s $NH_3$ pulses at 50-800 ppb. In particular, the source/drain current (VSD=-1V) versus time is shown, following a series of $NH_3$ gas pulses (10 s) at 50, 100, 200, 400 and 800 ppb in dry air at 96° C. The curves are offset for clarity Interestingly, both networks demonstrated very fast response times, which may be attributed to the network morphology—composed mainly of individualized nanotube with easily accessible surfaces. This may be expected for fully exposed SWCNT network prepared from decomposable polymers. For PFDD, only the aromatic backbone closely contacts with nanotube surface and at ~1/1 polymer/tube weight ratio, the surface coverage remains small, since more than 60% of the carbon content resides with the alkyl side chains. This may explain the difference in the lower detection limit between polymers after PBDTFTz decomposition.

Using the response curve from the 50 ppb $NH_3$ pulse, the detection limit for pristine SWCNTs and PFDD/SWCNTs networks was calculated at 2.5 and 9.3 ppb, respectively (considering the detectable response to be three times of the noise). Such sensitivity limits would make these SWCNT transistors suitable for medical applications. This high sensitivity may be attributed to the high purity of sc-SWCNTs obtained from the conjugated polymer extraction process, which reduces the unwanted current baseline from metallic nanotubes. Tracking the sensor response near the threshold voltage and adjusting gate bias to flatten the baseline may further improve sensitivity, thereby mitigating drift.

Figure 10:
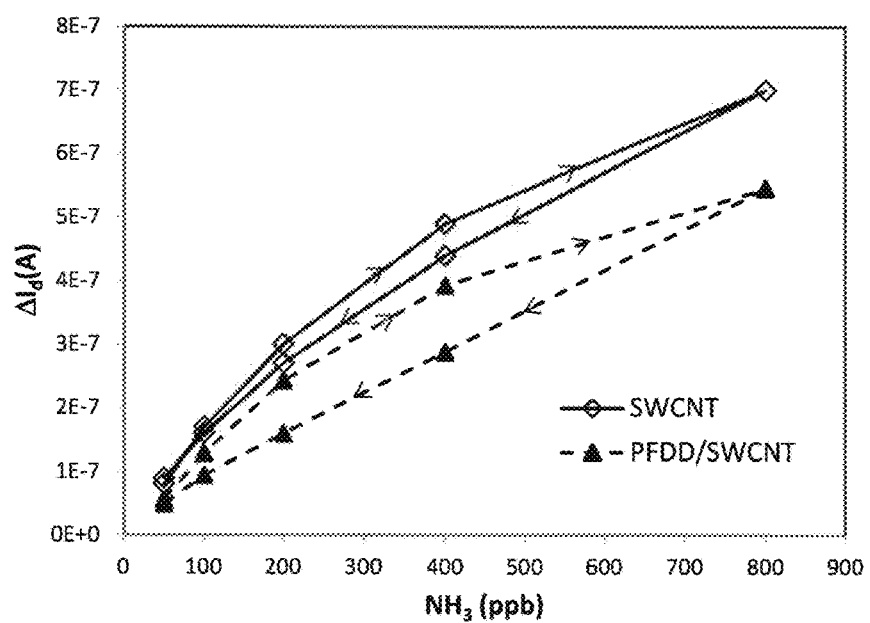
FIG. 10 illustrates a change of Source/Drain current at various NH3 concentration.

FIG. 10 shows the change of source/drain current at various $NH_3$ concentrations. Comparatively, a pristine SWCNT network (after PBDTFTz decomposition) presents stronger response towards NH3 pulses than a PFDD/SWCNT network. Moreover, upon cycling between low to high dosages, bare networks also have less hysteresis. Since the sensor response are often directly related to the surface area of SWCNTs, it is not surprising to find a stronger response with bare nanotubes. It is worth noting that the SWCNT networks are prepared from a simple dip-coating process that could easily be replicated using printing techniques such as gravure, ink-jet and aerosol spray. Comparatively, other reported networks for sensor applications having comparable performance were prepared from direct CVD growth process or unpurified tubes in chemiresistors.

REFERENCES

The contents of the entirety of each of which are incorporated by this reference:

P. Avouris, *Acc. Chem. Res.* 2002, 35, 1026.
Q. Cao, J. A. Rogers, *Adv. Mater.* 2009, 21, 29;
L. Hu, D. S. Hecht, G. Grüner, *Chem. Rev.* 2010, 110, 5790,
R. V. Noorden, *Nature* 2011, 469, 14.
C. Wang, K. Takei, T. Takahashi, A. Javey, *Chem. Soc. Rev.* 2013, 42, 2592.
M. F. L. De Voider, S. H. Tawfick, R. H. Baughman, A. J. Hart, *Science* 2013, 339, 535.
Q. Zhang, J. Q. Huang, W. Z. Qian, Y. Y. Zhang, F, Wei, *Small* 2013, 9, 1237,
L.-M. Peng, Z. Zhang, S. Wang, *Mater. Today,* 2014, 17, 434.
H. Zhang, B. Wu, W. Hu, Y. Liu, *Chem. Soc. Rev.,* 2011, 40, 1324,
F. Lu, M. J. Meziani, L. Cao, Y. P. Sun, *Langmuir* 2011, 27, 4339.
Y. Wu, X. Lin, M. Zhang, J. *Nanomaterials,* 2013, 627215.
A. D. Franklin, *Nature,* 498, 443.
D.-M. Sun, C. Liu, W. C. Ren, H.-M. Cheng, *Small* 2013, 9, 1188.
Y. Che, H. Chen, H. Gui, J. Liu, B. Liu, C. Zhou, *Semicond. Sci. Technol.* 2014, 29, 073001.
G. S. Tulevski, A. D. Franklin, D. Frank, J. M. Lobez, Q. Can, H. Park, A. Afzali, S.-J. Han, J. B. Hannon, W. Haensch, *ACS Nano,* 2014, 8, 8730.
T. Fujigaya, N. Nakashima, *Sci. Technol. Adv. Mater.* 2015, 16, 024802.
H, Wang, Z. Bao, *Nano Today,* 2015, 10, 737.
Z. Li, J. Ding, P. Finnie, J. Lefebvre, F. Cheng, C. T. Kingston, P. R. L. Malenfant, *Nano Res.* 2015, 8, 2179.
G. J. Brady, Y. Joo, S. S. Roy, P. Gopalan, M. S. Arnold, *Appl. Phys. Lett.* 2014, 104, 083107.

Z. Li, J. Ding, J. Lefebvre, P. R. L. Malenfant, *Org. Electron.* 2015, 26, 15.

C. M. Homenick, R. James, G. P. Lopinski, J. Dunford, J. Sun, H. Park, Y. Jung, G. Cho, P. R. L. Malenfant, *ACS Appl. Mater. Interfaces*, 2016, 8, 27900;

C. Cao, J. B. Andrews, A. D. Franklin, *Adv. Electron. Mater.* 2017, 3, 1700057.

F. Lemasson, J. Tittmann, F. Hennrich, N. Stürzl, S. Malik, M. M. Kappes, M Mayor, *Chem. Commun.* 2011, 47, 7428.

T. Umeyama, K. Kawabata, N. Tezuka, Y. Matano, Y. Miyato, K. Matsushige, Tsujimoto, S. Isoda, M. Takano, H. Imahori, *Chem. Commun.*, 2010, 46, 5969.

Z. Zhang, Y. Che, R. A. Smaldone, M. Xu, B. R. Bunes, J. S. Moore, L. Zang, *J. Am. Chem. Soc.* 2010, 132, 14113.

W. Z. Wang, W. F. Li, X. Y. Pan, C. M. Li, L.-J. Li, Y. G. Mu, J. A. Rogers, M. B. Chan-Park, *Adv. Funct. Mater.* 2011, 21, 1643.

Q. Ji, J. Han, X. Yu, S. Qiu, H. Jin, D. Zhang, Q. Li, *Carbon*, 2016, 105, 448.

I. Pochorovski, H, Wang, J. I. Feldblyum, X. Zhang, A. L. Antaris, Z. Bao, *J. Am. Chem. Soc.* 2015, 137, 4328.

F. Toshimitsu, N. Nakashima, *Sci. Rep.* 2015, 5, 18066, doi: 10.1038/srep18066.

A. Llanes-Pallas, K. Yoosaf, H. Traboulsi, J. Mohanraj, T. Seldrum, J. Dumont, A. Minoia, R. Lazzaroni, N. Armaroli, D. Bonifazi, *J. Am. Chem. Soc.* 2011, 133, 15412.

T. Lei, X. Chen, G. Pitner, H.-S. P. Wong, Z. Bao, *J. Am. Chem. Soc.* 2016, 138, 802.

F. Toshimitsu, N. Nakashima, *Nat. Commun.* 2014, 5:5041, doi: 10.1038/ncomms6041.

Y. Joo, G. J. Brady, M. J. Shea, M. B. Oviedo, C. Kanimozhi, S. K. Schmitt, B. M. Wong, M. S. Arnold, P. Gopalan, *ACS Nano* 2015, 9, 10203.

Z. Li, J. Ding, *Macromol. Chem. Phys.* 2011, 212, 2260.

Z. Li, J. Ding, N. Song, J. Lu, Y. Tao, *J. Am. Chem. Soc.* 2010, 132, 13160.

Z. Li, J. Ding, N. Song, X. Du, J. Zhou, J. Lu, Y. Tao, *Chem. Mater.* 2011, 23, 1977.

W. Gomulya, G. D. Costanzo, E. J. F. de Carvalho, S. Z. Bisri, V. Derenskyi, M. Fritsch, N. Fröich, S. Allard, P. Gordiichuk, A. Herrmann, S. J. Marrink, M. C. dos Santos, U. Scherf, M. A. Loi, *Adv. Mater.* 2013, 25, 2948.

J. Ding, Z. Li, J. Lefebvre, F. Cheng, G. Dubey, S. Zou, P. Finnie, A. Hrdina, L. Scoles, G. P. Lopinski, C. T. Kinsgton, B. Simard, P. R. L. Malenfant, *Nanoscale*, 2014, 6, 2328.

http://raymorcom/our-products/isosol-s100/, accessed: August, 2016,

S. D. Stranks, C.-K. Yong, J. A. Alexander-Webber, C. Weisspfennig, M. B. Johnston, L. M. Herz, R. J. Nicholas, *ACS Nano* 2012, 6, 6058.

S. D. Stranks, S. N. Habisreutinger, B. Dirks, R. J. Nicholas, *Adv. Mater.* 2013, 25, 4365.

S. D. Stranks, A. M. R. Baker, J. A. Alexander-Webber, B. Dirks, R. J. Nicholas. *Small*, 2013, 9, 2245.

T. Takenobu, T. Takano, M. Shiraishi, Y. Murakami, M. Ata, H. Kataura, Y. Achiba, Y. Iwasa, *Nat. Mater.* 2003, 2, 683.

Y. Joo, G. J. Brady, M. S. Arnold, R. Gopalan, *Langmuir* 2014, 30, 3460;

M. L. Geier, K. Moudgil, S. Barlow, S. R. Marder, M. C. Hersam, *Nano Lett.* 2016, 16, 4329.

M. J. Shea, R. D. Mehlenbacher, M. T. Zanni, M. S. Arnold, *J. Phys. Chem. Lett*, 2014, 5, 3742.

Q. Cao, S.-J. Han, G. S. Tulevski, A. D. Franklin, W. Haensch, *ACS Nano* 2012, 6, 6471.

J. M. Lobez, T. M. Swager, *Angew. Chem, Int Ed.* 2010, 49, 95.

A. Chortos, I. Pochorovski, P. Lin, G. Pitner, X. Yan, T. Z. Gao, J. W. F. To, T. Lei, J. W. Will III, H.-S. P. Wong, Z. Bao, *ACS Nano*, 2017, DOI: 10.1021/acsnano.7b01076.

G. J. Brady, A. J. Way, N. S. Safron, H. T. Evensen, P. Gopalan, M. S. Arnold, *Sci. Adv.* 2016, 2, e1601240.

R. Ihly, K. S. Mistry, A. J. Ferguson, T. T. Clikeman, B. W. Larson, O. Reid, O. V. Boltalina, S. H. Strauss, G. Rumbles, J. L. Blackburn, *Nat. Chem.* 2016, 8, 603.

M. L. Moser, G. Li, M, Chen, E. Bekyarova, M. E. Itkis, R. C. Haddon, *Nano Lett.* 2016, 16, 5386.

B. Norton-Bake, R. Ihly, I. E. Gould, A. D. Avery, Z. R. Owczarczyk, A. J. Ferguson, J. L. Blackburn, *ACS Energy Lett.* 2016, 1, 1212.

J. E. Ellis and A. Star, *ChemPlusChem*, 2016, 81, 1248-1265.

J. F. Fennell, Jr., S. F. Lui, J. M, Azzarelli, J. G. Weis, S. Rochat, K. A. Mirca, J. B. Ravnsboek, and T. M. Swager, *Angew. Chem. Int. Ed.* 2016, 55, 1266-1281.

T. Zhang, S. Mubeen, N. V. Myung and M. A Deshusses, *Nanotechnology* 19 (2008) 332001 (14 pp)

J. Kong, N. R. Franklin, C. Zhou, M. G. Chapline, S. Peng, K. Cho, H. Dai, *Science*, 2000, 287, 622.

C. M. Aguirre, P. L. Levesque, M. Paillet, F. Lapointe, B. C. St-Antoine, P. Desjardins, R. Martel, *Adv. Mater.* 2009, 21, 3087.

F. Rigoni, S. Tognolini, P. Borghetti, G. Drera, S. Pagliara, A. Goldoni, L Sangalefti, *Analyst*, 2013, 138, 7392.

G. Chen, T. M, Paronyan, E. M. Pigos, A. R. Harutyunyan, *Sci. Rep.* 2012, 2, 343; DOI:10.1038/srep00343.

X. Wang, G. Li, R. Liu, H. Ding, T. Zhang, J, *Mater. Chem.*, 2012, 22, 21824.

P. Qi, O. Vermesh, M. Grecu, A. Javey, Q. Wang, H. Dai, *Nano Lett.* 2003, 3, 347. M. Rother, M. Brohmann, S. Yang, S. B. Grimm, S. P. Schie☐l, A. Graf, J. Zaumseil, *Adv. Electron. Mater.* 2017, 1700080;

J. Lefebvre, J. Ding, *Mater. Today Comm.* 2017, 10, 72.

M. Meyyappan, *Small*, 2016, 12, No. 16, 2118-2129 http://raymorcom/our-products/isosol-s100/, accessed: August, 2016.

The novel features will become apparent to those of skill in the art upon examination of the description. It should be understood, however, that the scope of the claims should not be limited by the embodiments, but should be given the broadest interpretation consistent with the wording of the claims and the specification as a whole.

We claim:

1. A process for producing a chemical sensor that detects one or more chemicals in the ppt to ppb range, the process comprising:
   a) applying a dispersion of a sc-SWCNT/s-tetrazine based conjugated polymer composite to a substrate;
   b) applying heat and/or UV light to decompose the s-tetrazine based conjugated polymer; and
   c) removing the resulting decomposition products.

2. The process of claim 1, wherein the sensor has a lower detection limit of from 4 ppt to 100 ppb.

3. The process of claim 1, wherein the one or more chemicals is gaseous ammonia or gaseous nitrogen dioxide ($NO_2$).

4. The process of claim 1, wherein the s-tetrazine based polymer has the following structure:

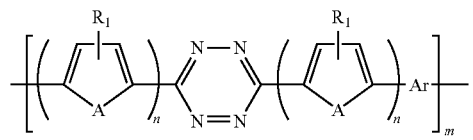

where A is O, S, Se or C=C; n is an integer from 1 to 4; $R_1$ is independently H, F, CN or a C1-C20 linear or branched aliphatic group; Ar is one or more substituted or unsubstituted aromatic units; and, m is an integer 5 or greater.

5. The process of claim 1, wherein the s-tetrazine based polymer is PBDTFTz:

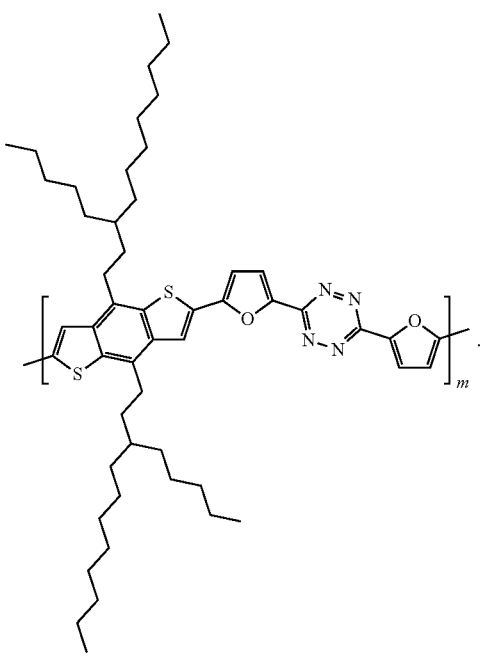

6. The process of claim 1, wherein the s-tetrazine based polymer is PDTSTTz:

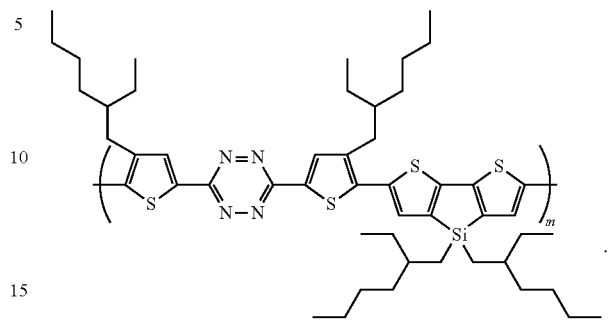

7. The process of claim 1, wherein the s-tetrazine based polymer is PCPDTFTz:

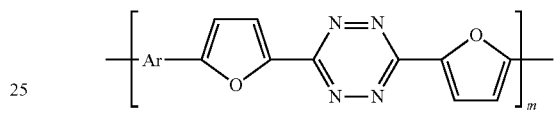

in which Ar=cyclopenta[2,1-b;3.4-b']dithiophene.

8. The process of claim 1, wherein the conjugated polymer comprises a polyfluorene or polythiophene.

* * * * *